United States Patent [19]

Branca et al.

[11] 4,374,773
[45] Feb. 22, 1983

[54] TRIAZOLO-BENZODIAZEPINE DERIVATIVES

[75] Inventors: Quirico Branca, Birsfelden; Albert E. Fischli, Riehen, both of Switzerland; André Szente, Dee Why, Australia

[73] Assignee: Hoffmann-La Roche Inc., Nutley, N.J.

[21] Appl. No.: 225,747

[22] Filed: Jan. 16, 1981

[30] Foreign Application Priority Data

Feb. 8, 1980 [CH] Switzerland .................. 1038/80

[51] Int. Cl.³ .................. A61K 31/55; C07D 487/04
[52] U.S. Cl. .................. 260/245.5; 260/244.4; 260/239.3 D; 424/267; 424/269; 564/195; 564/328
[58] Field of Search .................. 260/244.4, 245.5

[56] References Cited

U.S. PATENT DOCUMENTS 4,251,443  2/1981  Fischli et al. .................. 424/244

OTHER PUBLICATIONS

Moffett, Letters on Heterocyclic Chemistry, vol. III, pp. S-123-129 (1976).

Primary Examiner—Alton D. Rollins

Attorney, Agent, or Firm—Jon S. Saxe; Bernard S. Leon; Frank P. Hoffman

[57] ABSTRACT

There are presented compounds of the formula

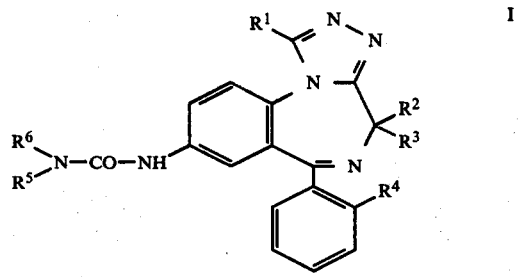

wherein $R^1$ is a hydrogen atom or a lower alkyl group, $R^2$ and $R^3$ each are a hydrogen atom or a lower alkyl group, $R^4$ is a halogen atom and either $R^5$ is a hydrogen atom or a lower alkyl group and $R^6$ is a lower alkyl or lower hydroxyalkyl group or $R^5$ and $R^6$ together with the nitrogen atom to which they are attached are a 3-membered to 7-membered heterocycle, and pharmaceutically acceptable acid addition salts thereof.

The compounds and their salts are novel and possess valuable pharmacodynamic properties.

15 Claims, No Drawings

TRIAZOLO-BENZODIAZEPINE DERIVATIVES

DESCRIPTION OF THE INVENTION

The present invention relates to benzodiazepine derivatives.

The benzodiazepine derivatives provided by the present invention are compounds of the formula

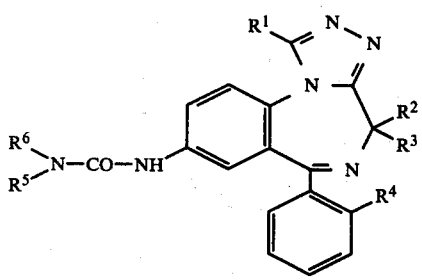

wherein $R^1$ is a hydrogen atom or a lower alkyl group, $R^2$ and $R^3$ each are a hydrogen atom or a lower alkyl group, $R^4$ is a halogen atom and either $R^5$ is a hydrogen atom or a lower alkyl group and $R^6$ is a lower alkyl or lower hydroxyalkyl group or $R^5$ and $R^6$ together with the nitrogen atom to which they are attached are a 3-membered to 7-membered heterocycle, and pharmaceutically acceptable acid addition salts thereof.

The aforementioned compounds and salts are novel and possess valuable pharmacodynamic properties.

Objects of the present invention are compounds of the foregoing formula I and pharmaceutically acceptable acid addition salts thereof per se and as pharmaceutically active substances, the manufacture of said compounds and salts, intermediates for the manufacture of said compounds, medicaments containing one or more compounds of formula I or pharmaceutically acceptable acid addition salts thereof, the manufacture of said medicaments as well as the use of compounds of formula I and of pharmaceutically acceptable acid addition salts thereof in the control or prevention of illnesses.

As used in this Specification, the term "lower alkyl", alone or in combination such as in "lower hydroxyalkyl" and the like, denotes straight-chain or branched-chain saturated hydrocarbon groups containing at most 7, preferably at most 4, carbon atoms such as methyl, ethyl, n-propyl, isopropyl, n-butyl, tert.butyl etc. The term "lower hydroxyalkyl" includes groups such as 2-hydroxyethyl, 3-hydroxy-2-propyl and the like. The term "halogen" means fluorine, chlorine, bromine or iodine. When $R^5$ and $R^6$ together with the nitrogen atom to which they are attached represent a 3-membered to 7-membered heterocycle, then there primarily come into consideration aziridine, pyrrolidine and piperidine groups. The term "lower alkylene" used herein denotes divalent saturated hydrocarbon groups which can be straight-chain or branched-chain and which contain at most 7, preferably at most 4, carbon atoms such as methylene, ethylene, 1,2-propylene, ethylidene and the like.

Among the compounds of formula I there are preferred those in which $R^1$ represents a hydrogen atom or a methyl group. $R^2$ and $R^3$ both preferably represent a hydrogen atom or both preferably represent a methyl group. $R^4$ preferably represents a fluorine or chlorine atom. $R^5$ and $R^6$ both preferably represent a methyl group or $R^5$ preferably represents a hydrogen atom and $R^6$ preferably represents a hydroxyethyl group or $R^5$ and $R^6$ together with the nitrogen atom to which they are attached preferably represent a pyrrolidinyl group.

Quite especially preferred compounds of formula I are:

1-[6-(o-Fluorophenyl)-1,4,4-trimethyl-4H-s-triazolo-[4,3-a][1,4]benzodiazepin-8-yl]-3-(2-hydroxyethyl)urea 1-[6-(o-chlorophenyl)-1,4,4-trimethyl-4H-s-triazolo-[4,3-a][1,4]benzodiazepin-8-yl]-3-(2-hydroxyethyl)urea, 3-[6-(o-fluorophenyl)-4,4-dimethyl-4H-s-triazolo-[4,3-a][1,4]benzodiazepin-8-yl]-1,1-dimethylurea, 3-[6-(o-chlorophenyl)-4H-s-triazolo[4,3-a][1,4]-benzodiazepin-8-yl]-1,1-dimethylurea, 3-[6-(o-chlorophenyl)-1-methyl-4H-s-triazolo[4,3-a]-[1,4]benzodiazepin-8-yl]-1,1-dimethylurea and N-[6-(o-chlorophenyl)-4,4-dimethyl-4H-s-triazolo[4,3-a][1,4]benzodiazepin-8-yl]-1-pyrrolidinecarboxamide.

Other compounds of formula I which are preferred are:

1-[6-(o-Fluorophenyl)-4H-s-triazolo[4,3-a][1,4]benzodiazepin-8-yl]-3-(2-hydroxyethyl)urea, 3-[6-(o-fluorophenyl)-4H-s-triazolo[4,3-a][1,4]benzodiazepin-8-yl]-1,1-dimethylurea, 1-[6-(o-fluorophenyl)-1-methyl-4H-s-triazolo-[4,3-a][1,4]benzodiazepin-8-yl]-3-(2-hydroxyethyl)urea, 3-[6-(o-fluorophenyl)-1,4,4-trimethyl-4H-s-triazolo-[4,3-a][1,4]benzodiazepin-8-yl]-1,1-dimethylurea, 1-[6-(o-chlorophenyl)-4H-s-triazolo[4,3-a][1,4]benzodiazepin-8-yl]-3-(2-hydroxyethyl)urea, 1-[6-(o-chlorophenyl)-1-methyl-4H-s-triazolo-[4,3-a][1,4]benzodiazepin-8-yl]-3-(2-hydroxyethyl)urea, N-[6-(o-chlorophenyl)-1-methyl-4H-s-triazolo-[4,3-a][1,4]benzodiazepin-8-yl]-1-pyrrolidinecarboxamide and N-[6-(o-fluorophenyl)-1,4,4-trimethyl-4H-s-triazolo-[4,3-a][1,4]benzodiazepin-8-yl]-1-pyrrolidinecarboxamide.

According to the process provided by the present invention, the benzodiazepine derivatives aforesaid (i.e. the compounds of formula I and their pharmaceutically acceptable acid addition salts) are manufactured by (a) reacting a benzodiazepine derivative of the formula

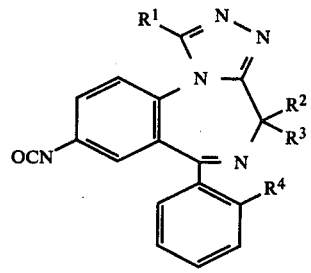

wherein $R^1$, $R^2$, $R^3$ and $R^4$ have the significance given earlier, with an amino compound of the formula

wherein $R^5$ and $R^6$ have the significance given earlier,
or (b) reacting a benzodiazepine derivative of the formula

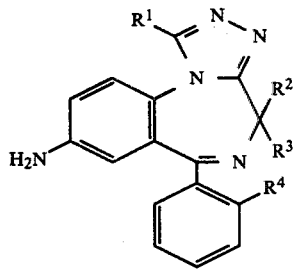

wherein $R^1$, $R^2$, $R^3$ and $R^4$ have the significance given earlier,
with a halide of the formula

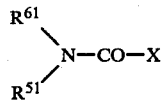

wherein X is a halogen atom and either $R^{51}$ and $R^{61}$ each are a lower alkyl group or $R^{51}$ and $R^{61}$ together with the nitrogen atom to which they are attached are 3-membered to 7-membered heterocycle,
or (c) reacting a benzodiazepine derivative of formula IV hereinbefore with an isocyanate of the formula $R^{62}$—NCO   VI wherein $R^{62}$ is a lower alkyl group,
or (d) removing the protecting group(s) from a benzodiazepine derivative of the formula

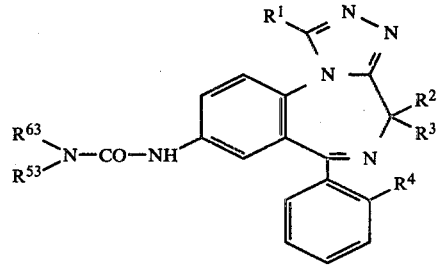

wherein $R^1$, $R^2$, $R^3$ and $R^4$ have the significance given earlier and either $R^{53}$ is a protecting group and $R^{63}$ is a lower alkyl group or a group of the formula

—A—O—Y   VIII in which A is a lower alkylene group and Y is a protecting group, or $R^{53}$ is a hydrogen atom or a lower alkyl group and $R^{63}$ is a group of formula VIII hereinbefore, or (e) converting a benzodiazepine derivative of the formula

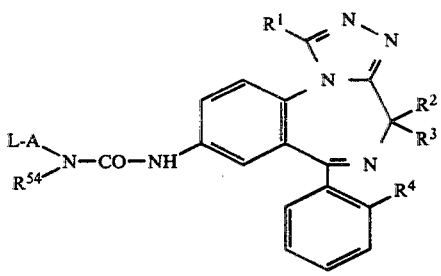

wherein $R^1$, $R^2$, $R^3$, $R^4$ and A have the significance given earlier, $R^{54}$ is a hydrogen atom or a lower alkyl group and L is a leaving group,
into a corresponding hydroxy compound,
or (f) hydrolytically opening the aziridine ring in a benzodiazepine derivative of the formula

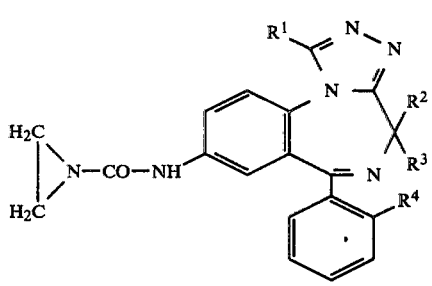

wherein $R^1$, $R^2$, $R^3$ and $R^4$ have the significance given earlier,
or (g) converting a compound of formula I into a pharmaceutically acceptable acid addition salt.

According to embodiment (a) of the process, the compounds of formula I can be manufactured from benzodiazepine derivatives of formula II and amino compounds of formula III. In this case, the compound of formula II is conveniently prepared in the manner described hereinafter from the corresponding benzodiazepine derivative of formula IV shortly or immediately before the reaction with the amino compound of formula III and is introduced into the reaction not in isolated form but in the solution in which it has previously been prepared from the corresponding benzodiazepine derivative of formula IV.

An amino compound of formula III can then be added to the aforementioned solution containing the benzodiazepine derivative of formula II. In so doing, the amino compound of formula III can be used in the form of a solution or in the absence of a solvent. Where an amino compound which is gaseous at room temperature is used (e.g. in the case of methylamine), it can be introduced as the gas into the aforementioned solution containing the benzodiazepine derivative of formula II.

On the other hand, it is also possible to provide the amino compound of general formula III, conveniently in the form of a solution, and then to add thereto the aforementioned solution containing the benzodiazepine derivative of formula II. In many cases it is convenient to use an excess of the amino compound of formula III.

Various organic solvents which are inert under the reaction conditions (e.g. halogenated hydrocarbons such as dichloroethane, methylene chloride, chloroform, o-dichlorobenzene etc., ethers such as tetrahydrofuran, dioxan, dimethoxyethane, diethyleneglycol dimethyl ether etc. or the like) are suitable as the solvent for embodiment (a) of the process.

The reaction of a compound of formula II with an amino compound of formula III is conveniently carried out at room temperature or at a temperature below room temperature. When the amino compound of formula III is added to a solution of the benzodiazepine derivative of formula II, the addition should be performed within a short time, whereas in the opposite case (i.e. when the solution of the benzodiazepine derivative of formula II is added to the amino compound of formula III) the promptness with which the addition is carried out is not critical.

According to embodiment (b) of the process, compounds of formula I can be manufactured by reacting a benzodiazepine derivative of formula IV with a halide of formula V. The reaction is carried out in the presence of an acid-binding agent; for example, an inorganic base such as potassium carbonate, sodium carbonate etc. or an organic base such as a tertiary amino compound (e.g. triethylamine, N-ethyldiisopropylamine, quinuclidine etc.)

The reaction of a benzodiazepine derivative of formula IV with a halide of formula V is conveniently carried out at room temperature or at a temperature below room temperature. The reaction proceeds relatively slowly and generally takes several days.

According to embodiment (c) of the process, compounds of formula I can be manufactured by reacting a benzodiazepine derivative of formula IV with an isocyanate of formula VI. This reaction is conveniently carried out in an organic solvent which is inert under the reaction conditions; for example, a halogenated hydrocarbon such as methylene chloride, dichloroethane, chloroform, o-dichlorobenzene etc., an ether such as tetrahydrofuran, dioxan, dimethoxyethane, diethyleneglycol dimethyl ether etc. or the like. In many cases it has been found to be favourable to carry out the reaction in the presence of a catalytically-acting small amount of a base; for example, a tertiary amino compound such as triethylamine, N-ethyl-diisopropylamine, quinuclidine etc. The temperature at which this reaction is carried out is not critical and the reaction can be carried out at room temperature, at a temperature below room temperature or at a temperature above room temperature (e.g. at the reflux temperature).

According to embodiment (d) of the process, compounds of formula I can be manufactured by removing the protecting group or the protecting groups from a benzodiazepine derivative of formula VII. Suitable nitrogen-protecting groups for the purpose of the present invention are primarily acyl groups, preferably readily cleavable alkoxycarbonyl or aralkoxycarbonyl groups, especially tert.butoxycarbonyl, benzyloxycarbonyl etc. as well as readily cleavable aralkyl groups such as benzyl. Suitable oxygen-protecting groups are on the one hand acyl groups or aralkyl groups such as those mentioned earlier as nitrogen-protecting groups and on the other hand ketal protecting groups such as tetrahydropyranyl, 2-methoxy-2-propyl, methoxymethyl, β-methoxyethoxy-methyl etc. or readily cleavable alkyl groups such as tert-butyl etc. or alkanoyl groups such as acetyl and the like.

The removal of the protecting group or of the protecting groups from the benzodiazepine derivatives of formula VII is carried out according to methods known per se, whereby, of course, the nature of the protecting group or protecting groups to be removed must be taken into consideration when choosing the method or methods used for the removal. In addition, it will, of course, be appreciated that only those methods can be used which selectively remove the protecting group or protecting groups without affecting other structural elements present in the molecule.

The groups mentioned earlier as examples of protecting groups can be cleaved off, depending on their nature, hydrogenolytically and/or hydrolytically. Thus, for example, the benzyloxycarbonyl group and the tert.butoxycarbonyl group can be cleaved off under selective acidic conditions; for example, by treatment with a mixture of hydrogen bromide and glacial acetic acid or by treatment with boron trifluoride or boron tribromide in an inert organic solvent such as dichloromethane. The tert-butoxycarbonyl group can also be cleaved off by treatment with hydrogen chloride in an inert organic solvent such as dioxan, tetrahydrofuran or the like or by treatment with trifluoroacetic acid. The tetrahydropyranyl group can be cleaved off under mild acidic conditions; for example, by treatment with a dilute aqueous mineral acid under mild conditions. The tert.butyl group can be cleaved off, for example, using trifluoroacetic acid. The benzyl group can be cleaved off by catalytic hydrogenation (e.g. over palladium/carbon). The acetyl group can be cleaved off under mild alkaline conditions; for example, with a solution of a sodium alcoholate in a corresponding alcohol (e.g. methanolic sodium methylate).

According to embodiment (e) of the process, compounds of formula I can be manufactured by converting a benzodiazepine derivative of formula IX into a corresponding hydroxy compound. The leaving group denoted by L in formula IX can be a halogen atom, especially a chlorine, bromine or iodine atom, or an equivalent leaving group (e.g. an arylsulphonyloxy group such as tosyloxy, an alkylsulphonyloxy group such as mesyloxy, a quaternary ammonium group such as the trimethylammonium group etc.)

The conversion of a benzodiazepine derivative of general formula IX into a corresponding hydroxy compound can be carried out, for example, by solvolysis in a water-containing system, conveniently in a mixture of an aromatic hydrocarbon (e.g. benzene) and water in the presence of a quaternary ammonium salt (e.g. tetrabutylammonium bromide) and at a temperature between room temperature and the reflux temperature of the mixture.

According to embodiment (f) of the process, compounds of formula I can be manufactured by hydrolytically opening the aziridine ring in benzodiazepine derivatives of formula Ia. This hydrolytic ring-opening is carried out under acidic conditions, there coming into consideration only those acids whose anion does not react with the aziridine ring. The hydrolytic ring-opening is conveniently carried out at room temperature in the presence of a suitable organic solvent which is inert under the reaction conditions. For example, the hydrolytic ring-opening can be carried out by dissolving the benzodiazepine derivative of formula Ia in dioxan or the like, adding to the solution a small amount of a mineral acid (e.g. a few drops of 25 percent sulphuric acid) and leaving the mixture to stand for a further short time (e.g. 15 to 30 minutes).

According to embodiment (g) of the process, the compounds of formula I can be converted into pharmaceutically acceptable acid addition salts. The manufacture of such pharmaceutically acceptable acid addition salts is carried out according to customary methods. There come into consideration not only salts with inorganic acids but also salts with organic acids; for example, hydrochlorides, hydrobromides, sulphates, citrates, acetates, succinates, methanesulphonates, p-toluenesulphonates and the like.

The benzodiazepine derivatives of formula II used as starting materials in embodiment (a) of the process can be prepared, as mentioned earlier, from corresponding benzodiazepine derivatives of formula IV, namely by reaction with phosgene. In this case, conveniently a solution of a benzodiazepine derivative of formula IV is added to a solution of phosgene in an organic solvent which is inert under the reaction conditions while cooling, the mixture is heated to boiling under reflux for a period, again cooled down and finally the solution obtained is made basic or at least neutral with a tertiary organic amino compound such as triethylamine. The resulting solution, containing a benzodiazepine derivative of formula II, can be stored for several hours with the exclusion of moisture and in the cold; it is, as mentioned earlier, used directly in the process without isolation of the benzodiazepine derivative of formula II contained therein.

The benzodiazepine derivatives of formula II are also an object of the present invention. A representative benzodiazepine derivative of formula II is [6-(o-fluorophenyl)-4H-s-triazolo[4,3-a][1,4]benzodiazepin-8-yl]isocyanate.

The benzodiazepine derivatives of formula IV used as starting materials in embodiment (b) of the process belong to a class of compound known per se. Representatives which have not previously been specifically described can be prepared according to methods known per se and familiar to any person skilled in the art; for example, starting from compounds of formula X as illustrated in the following Reaction Scheme in which $R^1$, $R^2$, $R^3$ and $R^4$ have the significance given earlier:

Reaction Scheme

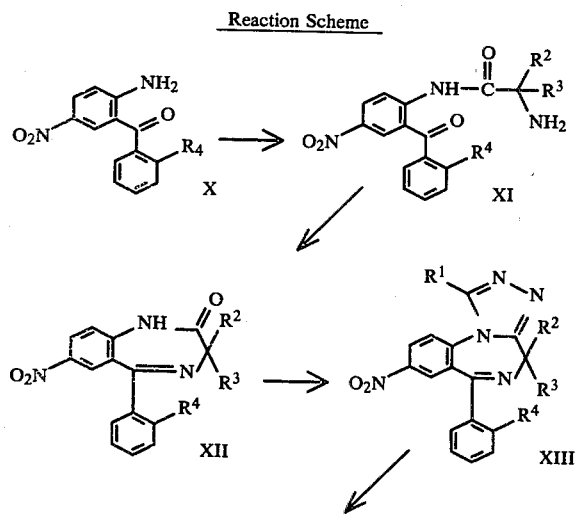

-continued
Reaction Scheme

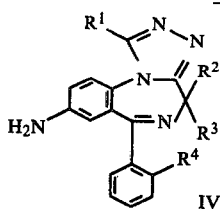

Various Examples hereinafter contain detailed information concerning the manufacture of certain benzodiazepine derivatives of formula IV.

Benzodiazepine derivatives of formula VII used as starting materials in embodiment (d) of the process can be prepared from benzodiazepine derivatives of formulae II or IV according to various methods known per se. It will, of course, be appreciated that the nature of the protecting group or protecting groups whose presence is desired in the benzodiazepine derivative of formula VII to be prepared must be taken into consideration when choosing the method or methods used.

For the preparation of a benzodiazepine derivative of formula VII in which $R^{53}$ represents a protecting group, a benzodiazepine derivative of formula IV can be reacted with a corresponding carbamoyl halide (in analogy to the method described earlier for the manufacture of compounds of formula I from benzodiazepine derivatives of formula IV and halides of formula V).

For the preparation of benzodiazepine derivatives of formula VII in which $R^{53}$ represents a hydrogen atom and $R^{63}$ represents a group of formula VIII, a benzodiazepine derivative of formula IV can be reacted with a corresponding isocyanate (in analogy to the method described earlier for the manufacture of compounds of formula I from benzodiazepine derivatives of formula IV and isocyanates of formula VI). A further possibility consists in reacting a benzodiazepine derivative of formula II with a corresponding amine (in analogy to the method described earlier for the manufacture of compounds of formula I from benzodiazepine derivatives of formula II and amino compounds of formula III). In this case, however, it will be appreciated that the protecting group denoted by Y can not be an acyl group. Furthermore, the aziridine ring in a benzodiazepine derivative of formula Ia can be opened by acid alcoholysis with tert.butanol, benzyl alcohol or the like to give a benzodiazepine derivative of formula VII in which $R^{53}$ represents a hydrogen atom and $R^{63}$ represents a 2-tert.butoxyethyl, 2-benzyloxyethyl or like group.

For the preparation of benzodiazepine derivatives of formula VII in which $R^{53}$ represents a lower alkyl group and $R^{63}$ represents a group of formula VIII, a benzodiazepine derivative of formula IV can be reacted with a corresponding carbamoyl halide (in analogy to the method described earlier for the manufacture of compounds of formula I from benzodiazepine derivatives of formula IV and halides of formula V). Another possibility consists in reacting a benzodiazepine derivative of formula II with a corresponding amine (in analogy to the method described earlier for the manufacture of compounds of formula I from benzodiazepine derivatives of formula II and amino compounds of formula III). Again, in this case, the protecting group denoted by Y can not be an acyl group.

The benzodiazepine derivatives of formula VII are also an object of the present invention.

Benzodiazepine derivatives of formula IX used as starting materials in embodiment (e) of the process can be prepared according to methods known per se from benzodiazepine derivatives of formula IV by reaction with a corresponding carbamoyl chloride (in analogy to the method described earlier for the manufacture of compounds of formula I from benzodiazepine derivatives of formula IV and halides of formula V) when $R^{54}$ represents a lower alkyl group, or by reaction with a corresponding isocyanate (in analogy to the method described earlier for the manufacture of compounds of formula I from benzodiazepine derivatives of formulae IV and isocyanates of formula VI) when $R^{54}$ represents a hydrogen atom.

The benzodiazepine derivatives of formula IX are also an object of the present invention.

emptied. The spontaneously excreted urine and the remaining urine obtained at the conclusion of the experiment by pressing-out the urinary bladders are collected in graduated centrifuge glasses. Sodium and potassium concentrations in the urine are determined with a flame photometer.

The following Table contains results which have been obtained in the previously described experiment with representative compounds of formula I. In this Table there are given for each compound in question the dosage administered (in mg/kg p.o.) as well as the percentage variation in the urine volume, the sodium excretion and the potassium excretion in comparison with the control animals (i.e. in comparison with the animals treated only with aldosterone). Moreover, the Table contains data relating to the acute toxicity of the compounds investigated (LD 50 in mg/kg in the case of single oral administration to mice).

| $R^1$ | $R^2$ | $R^3$ | $R^4$ | $R^5$ | $R^6$ | Dosage mg/kg/p.o. | Volume in %, based on control animals | $[Na^{\oplus}]$ | $[K^{\oplus}]$ | LD 50 mg/kg/p.o. |
|---|---|---|---|---|---|---|---|---|---|---|
| H | $CH_3$ | $CH_3$ | F | $CH_3$ | $CH_3$ | 1 | 106 | 238 | 65 | >5000 |
| $CH_3$ | $CH_3$ | $CH_3$ | F | H | $CH_2CH_2OH$ | 1 | 112 | 256 | 90 | >5000 |
| H | H | H | Cl | $CH_3$ | $CH_3$ | 10 | 131 | 252 | 100 | >5000 |
| $CH_3$ | H | H | Cl | $CH_3$ | $CH_3$ | 10 | 103 | 252 | 112 | >5000 |
| H | $CH_3$ | $CH_3$ | Cl | $-CH_2-$ | $-CH_2-CH_2-CH_2-$ | 1 | 97 | 155 | 72 | >5000 |
| $CH_3$ | $CH_3$ | $CH_3$ | Cl | H | $CH_2CH_2OH$ | 1 | 75 | 215 | 75 | >5000 |

Surprisingly, it has been shown that the compounds of formula I and their pharmaceutically acceptable acid addition salts display no activity or only very slight activity on the central nervous system, whereas they exhibit pronounced aldosterone-antagonistic properties. These aldosterone-antagonistic properties can be demonstrated in adrenalectomised rats as illustrated hereinafter.

If aldosterone is administered to adrenalectomised rats, then there is observed, in comparison to untreated animals, a pronounced reduction of the sodium excretion (sodium retention), an increased potassium excretion (potassium excretion) as well as a reduction of the excreted urine volume. If compounds of formula I are administered to the animals before the treatment with aldosterone, then there is observed, in comparison with animals which are treated only with aldosterone (control animals), a pronounced increase of the sodium excretion (i.e. the sodium retention caused by aldosterone is antagonised), whereas the potassium excretion and the urine volume are influenced to a lesser extent.

The standard experiment is carried out as follows:

Female Holtzmann rats (150–180 g) are bilaterally adrenalectomised 70 to 74 hours before the beginning of the experiment. After the operation, the animals receive a customary rat dry feed and 0.9 percent sodium chloride solution for drinking. 16 to 17 hours before the beginning of the experiment the feed is removed from the animals, but they can subsequently drink, as before, 0.9 percent sodium chloride solution ad libitum. At the beginning of the experiment the substance to be tested as an aldosterone-antagonist is administered to the animals by means of a stomach probe. 30 minutes later the animals receive a subcutaneous injection of 4 mmg/kg of aldosterone. After a further 90 minutes, the urinary bladders of the animals are emptied by careful suprapubic pressure, whereupon the animals are placed individually in metabolic cages without food and without drink. The urine of the animals is then collected for 3 hours, whereupon their urinary bladders are once more The compounds of formula I and their pharmaceutically acceptable acid addition salts can be used as medicaments, for example, in the form of pharmaceutical preparations. The pharmaceutical preparations can be administered orally, for example in the form of tablets, coated tablets, dragees, hard and soft gelatin capsules, solutions, emulsions or suspensions. The administration can, however, also be carried out by the rectal route (e.g. in the form of suppositories) or by the parenteral route (e.g. in the form of injection solutions).

For the manufacture of tablets, coated tablets, dragees and hard gelatin capsules, the compounds of formula I and their pharmaceutically acceptable acid addition salts can be processed with pharmaceutical inert, inorganic or organic excipients. Examples of such excipients which can be used for tablets, dragees and hard gelatin capsules are lactose, maize starch or derivatives thereof, talc, stearic acid or salts thereof etc.

Suitable excipients for soft gelatin capsules are vegetable oils, waxes, fats, semi-solid and liquid polyols etc. Depending on the nature of the active ingredient, no excipients are, however, generally necessary in the case of soft gelatin capsules.

Suitable excipients for the manufacture of solutions and syrups are, for example, water, polyols, saccharose, invert sugar, glucose and the like.

Suitable excipients for injection solutions are, for example, water, alcohols, polyols, glycerine, vegetable oils etc.

Suitable excipients for suppositories are, for example, natural or hardened oils, waxes, fats, semi-liquid or liquid polyols and the like.

The pharmaceutical preparations can, moreover, contain preserving agents, solubilising agents, stabilising agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing one or more compounds of formula I or pharmaceutically acceptable acid addition salts thereof are also an object of the present invention as is a process for the manufacture of such medicaments, which process comprises bringing one or more compounds of formula I or pharmaceutically acceptable acid addition salts thereof and, if desired, one or more other therapeutically valuable substances into a galenical administration form. A further object of the present invention is, as mentioned earlier, the use of compounds of formula I and of pharmaceutically acceptable acid addition salts thereof in the control or prevention of illnesses, especially in the control or prevention of heart failure, of hepatic ascites, of primary aldosteronism and of idiopathic hypertension. The dosage can vary within wide limits and is, of course, adjusted to the individual requirements in each particular case. In general, in the case of oral administration a daily dosage of about 20 mg to 1500 mg should be appropriate.

The following Examples illustrate the present invention, but are not intended to limit its extent:

EXAMPLE 1

(a) 6 g (20.5 mmol) of 8-amino-6-(o-fluorophenyl)-4H-s-triazolo[4,3-a][1,4]benzodiazepine are brought into solution in 600 ml of 1,2-dichloroethane under reflux. 3.3 g (33.3 mmol) of phosgene, dissolved in 50 ml of ice-cold 1,2-dichloroethane, are placed in a sulphonation flask. The hot dichloroethane solution of the 8-amino-6-(o-fluorophenyl)-4H-s-triazolo[4,3-a][1,4]benzodiazepine is then added dropwise thereto while cooling with ice and stirring in such a manner that the temperature does not exceed 20° C. Subsequently, the mixture is heated at reflux for 1 hour while stirring, 100 ml of dichloroethane are distilled off and then the mixture is treated with 100 ml of fresh dichloroethane. While cooling with ice, argon is conducted directly into the solution until it reaches a temperature of 10° C. The thus-obtained dichloroethane solution of [6-(o-fluorophenyl)-4H-s-triazolo[4,3-a][1,4]benzodiazepin-8-yl]isocyanate is processed without isolation of the isocyanate contained therein.

(b) A suspension of 7.8 g (73.6 mmol) of sodium carbonate in 3.7 ml (61.6 mmol) of ethanolamine and 60 ml of acetonitrile is added in one portion while cooling with ice and stirring to the isocyanate solution prepared as described in paragraph (a). The mixture is stirred at room temperature for 20 hours and then concentrated at 50° C. on a rotary evaporator. The residue is treated with 500 ml of water and extracted several times with methylene chloride/ethanol (4:1). The combined organic extracts are dried over magnesium sulphate and concentrated. Crystallisation from ethanol yields 1-[6-(o-fluorophenyl)-4H-s-triazolo[4,3-a][1,4]benzodiazepin-8-yl]-3-(2-hydroxyethyl)urea of melting point 155° C. (decomposition).

EXAMPLE 2

(a) A dichloroethane solution of [6-(o-fluorophenyl)-4H-s-triazolo[4,3-a][1,4]benzodiazepin-8-yl]isocyanate is prepared as described in paragraph (a) of Example 1 from 5 g (17.05 mmol) of 8-amino-6-(o-fluorophenyl)-4H-s-triazolo-[4,3-a][1,4]benzodiazepine.

(b) To the foregoing isocyanate solution is added in one portion while cooling with ice and stirring a suspension of 6.5 g (61.3 mmol) of sodium carbonate in 5.2 g (115.6 mmol) of dimethylamine and 50 ml of ice-cold dichloroethane. After 20 hours at room temperature, the mixture is concentrated at 50° C. in vacuo, the residue is suspended in 300 ml of water and extracted four times with methylene chloride/ethanol (4:1). The combined organic extracts are washed with water, dried and concentrated. Crystallisation of the residue from methylene chloride/ethyl acetate yields 3-[6-(o-fluorophenyl)-4H-s-triazolo[4,3-a][1,4]benzodiazepin-8-yl]-1,1-dimethylurea of melting point 206° C. (decomposition).

EXAMPLE 3

A dichloroethane solution of [6-(o-fluorophenyl)-1-methyl-4H-s-triazolo[4,3-a][1,4]benzodiazepin-8-yl]isocyanate, prepared as described in paragraph (a) of Example 1 from 5 g (16.3 mmol) of 8-amino-6-(o-fluorophenyl)-1-methyl-4H-s-triazolo[4,3-a][1,4]benzodiazepine, is added dropwise at room temperature while stirring to a suspension of 6.2 g (58.5 mmol) of sodium carbonate in 3 ml (49.8 mmol) of ethanolamine and 40 ml of acetonitrile. After 20 hours, the mixture is partitioned between 500 ml of water and 500 ml of methylene chloride/ethanol (4:1) at 50° C. The separated aqueous phase is treated again in an analogous manner, the combined organic extracts are dried and concentrated in vacuo. Crystallisation of the residue from ethanol yields 1-[6-(o-fluorophenyl)-1-methyl-4H-s-triazolo[4,3-a][1,4]-benzodiazepin-8-yl]-3-(2-hydroxyethyl)urea of melting point 228°–230° C.

EXAMPLE 4

(a) 42.3 g (0.41 mol) of α-aminoisobutyric acid and 50 ml (0.68 mol) of thionyl chloride in 400 ml of tetrahydrofuran are stirred vigorously at room temperature for 24 hours, treated with 100 g (0.38 mol) of 2-amino-5-nitro-2'-fluorobenzophenone and stirred at room temperature for a further 108 hours. The mixture is concentrated in vacuo, poured into 500 ml of ice-cold 10 percent sodium bicarbonate solution and extracted with methylene chloride. After washing the organic phase with sodium bicarbonate solution and water, the solvent is removed in vacuo and the crude 2-amino-2'-(o-fluorobenzoyl)-2-methyl-4'-nitropropionanilide remaining is further processed directly.

(b) 184 g of the foregoing crude product in 1 liter of toluene and 100 ml of glacial acetic acid are heated to boiling under reflux for 21 hours in a water separator and subsequently evaporated to dryness in vacuo. The residue is suspended in 500 ml of boiling ether and filtered off. There is obtained 5-(o-fluorophenyl)-1,3-dihydro-3,3-dimethyl-7-nitro-2H-1,4-benzodiazepin-2-one of melting point 241° C.

(c) 55.25 g (0.16 mol) of 5-(o-fluorophenyl)-1,3-dihydro-3,3-dimethyl-7-nitro-2H-1,4-benzodiazepin-2-one, dissolved in 800 ml of tetrahydrofuran, are treated portionwise and while stirring at room temperature with 9.7 g of a 55 to 60 percent sodium hydride dispersion and the mixture is stirred at 50° C. for a further 60 minutes. 100 g (0.39 mol) of dimorpholinochlorophosphate are added to the cooled solution and the mixture is stirred at room temperature for 24 hours. After the addition of 50 g (0.67 mol) of acetic acid hydrazide, the mixture is stirred at room temperature for a further 45 hours and concentrated in vacuo. The residue is taken up in methylene chloride; the organic phase is washed with water and the solvent is removed. The residue is treated with 1.2 liters of n-butanol and heated to boiling under reflux. After distilling off 350 ml of solvent, the mixture remaining is heated at reflux for a further 1 hour and concentrated in vacuo. The residue is dissolved in 250 ml of hot ethanol. After cooling to −10° C., there is obtained crystalline 6-(o-fluorophenyl)-1,4,4-trimethyl-8-nitro-4H-s-triazolo[4,3-a][1,4]benzodiazepine of melting point 195° C.

(d) 43.6 g (0.12 mol) of 6-(o-fluorophenyl)-1,4,4-trimethyl-8-nitro-4H-s-triazolo[4,3-a][1,4]benzodiazepine in 600 ml of concentrated hydrochloric acid are treated portionwise with a total of 80.55 g (0.36 mol) of tin chloride in such a manner that the temperature of the mixture does not exceed 85° C. Subsequently, the mixture is stirred at room temperature for 1 hour, cooled to 0° C. and cautiously neutralised with 900 ml of 10 N sodium hydroxide. After extracting the remaining suspension three times with methylene chloride, the combined organic phases are washed with saturated sodium chloride solution, dried and evaporated. Recrystallisation of the residue from 350 ml of ethanol at −30° C. gives 8-amino-6-(o-fluorophenyl)-1,4,4-trimethyl-4H-s-triazolo[4,3-a][1,4]benzodiazepine of melting point 294° C.

(e) From 7.0 g (20.9 mmol) of 8-amino-6-(o-fluorophenyl)-1,4,4-trimethyl-4H-s-triazolo[4,3-a][1,4]benzodiazepine there is obtained in analogy to the procedure described in Example 1, via [6-(o-fluorophenyl)-1,4,4-trimethyl-4H-s-triazolo[4,3-a][1,4]benzodiazepin-8-yl]isocyanate, 1-[6-(o-fluorophenyl)-1,4,4-trimethyl-4H-s-triazolo[4,3-a][1,4]benzodiazepin-8-yl]-3-(2-hydroxyethyl)urea. After recrystallisation from acetonitrile, the product melts at 233° C.

EXAMPLE 5

(a) 8.75 g of a 55 to 60 percent sodium hydride dispersion (0.36 M) are added portionwise and while stirring at room temperature to a solution of 49.5 g (0.15 mol) of 5-(o-fluorophenyl)-1,3-dihydro-3,3-dimethyl-7-nitro-2H-1,4-benzodiazepin-2-one [prepared as described in paragraphs (a) and (b) of Example 4] in 800 ml of tetrahydrofuran and the mixture is stirred at 50° under argon for a further 1 hour. After cooling to room temperature, 96.6 g (0.39 mol) of dimorpholinochlorophosphate are added and the mixture is stirred at the same temperature for 20 hours. After the addition of 48.5 g (0.80 mol) of formylhydrazine, the mixture is stirred at room temperature under argon for 24 hours, concentrated in vacuo and the residue is taken up in methylene chloride. The organic phase is washed with water and dried. After removal of the solvent, the residue is taken up in 1 liter of n-butanol and heated to boiling. After distilling off 400 ml of solvent, the mixture remaining is heated at reflux for a further 1 hour, the solvent is removed in vacuo and the residue is filtered over 800 l g of silica gel using ethyl acetate/ethanol (9:1) for the elution. The thus-obtained crude product gives, after recrystallisation from ethanol, 6-(o-fluorophenyl)-4,4-dimethyl-8-nitro-4H-s-triazolo[4,3-a][1,4]benzodiazepine of melting point 235° C.

(b) 22.6 g (64.5 mmol) of 6-(o-fluorophenyl)-4,4-dimethyl-8-nitro-4H-s-triazolo[4,3-a][1,4]benzodiazepine, dissolved in 200 ml of concentrated hydrochloric acid, are treated portionwise with a total of 43.66 g (0.19 mol) of tin chloride in such a manner that the temperature does not exceed 85° C. The mixture is stirred at room temperature for a further 1 hour, cautiously neutralised with 10 N sodium hydroxide while cooling with ice and extracted with chloroform/ethanol (9:1) in a perforator. After removing the solvent, the residue is suspended in hot ethyl acetate and filtered off, there being obtained 8-amino-6-(o-fluorophenyl)-4,4-dimethyl-4H-s-triazolo[4,3-a][1,4]benzodiazepine of melting point 288° C.

(c) From a dichloroethane solution of [6-(o-fluorophenyl)-4,4-dimethyl-4H-s-triazolo[4,3-a][1,4]benzodiazepin-8-yl]isocyanate, prepared as described in paragraph (a) of Example 1 from 7.0 g (21.8 mmol) of 8-amino-6-(o-fluorophenyl)-4,4-dimethyl-4H-s-triazolo[4,3-a][1,4]benzodiazepine, there is obtained in analogy to the procedure described in paragraph (b) of Example 2 3-[6-(o-fluorophenyl)-4,4-dimethyl-4H-s-triazolo[4,3-a][1,4]benzodiazepin-8-yl]-1,1-dimethylurea. After recrystallisation from cold methylene chloride, the product melts at 180° C. (decomposition).

EXAMPLE 6

From a dichloroethane solution of [6-(o-fluorophenyl)-1,4,4-trimethyl-4H-s-triazolo[4,3-a][1,4]benzodiazepin-8-yl]isocyanate, prepared as described in paragraph (a) of Example 1 from 7.0 g (20.9 mmol) of 8-amino-6-(o-fluorophenyl)-1,4,4-trimethyl-4H-s-triazolo[4,3-a][1,4]benzodiazepine, there is obtained in analogy to the procedure described in paragraph (b) of Example 2 3-[6-(o-fluorophenyl)-1,4,4-trimethyl-4H-s-triazolo[4,3-a][1,4]benzodiazepin-8-yl]-1,1-dimethylurea. After recrystallisation from methylene chloride/toluene, the product melts at 285°–286° C.

EXAMPLE 7

(a) A solution of [6-(o-chlorophenyl)-4H-s-triazolo[4,3-a][1,4]benzodiazepin-8-yl]isocyanate is prepared as described in paragraph (a) of Example 1 from 7.0 g (22.6 mmol) of 8-amino-6-(o-chlorophenyl)-4H-s-triazolo-[4,3-a][1,4]benzodiazepine, but using methylene chloride in place of 1,2-dichloroethane.

(b) To the foregoing isocyanate solution is added in one portion and while stirring at room temperature a suspension of 8.7 g (81.9 mmol) of sodium carbonate in 4.9 ml (67.8 mmol) of ethanolamine and 60 ml of acetonitrile. The mixture is left for 20 hours at room temperature and then concentrated at 50° C. in vacuo. The residue is taken up in methylene chloride/ethanol (4:1), the organic phase is washed with water, dried and concentrated. After crystallisation from ethanol, there is obtained 1-[6-(o-chlorophenyl)-4H-s-triazolo[4,3-a][1,4]benzodiazepin-8-yl]-3-(2-hydroxyethyl)urea of melting point 228° C. (decomposition).

EXAMPLE 8

To a solution of [6-(o-chlorophenyl)-4H-s-triazolo[4,3-a][1,4]benzodiazepin-8-yl]isocyanate, prepared as described in paragraph (a) of Example 1 from 7.0 g (22.6 mmol) of 8-amino-6-(o-chlorophenyl)-4H-s-triazolo[4,3-a][1,4]benzodiazepine, but using methylene chloride in place of 1,2-dichloroethane, is added in one portion while cooling with ice and stirring a suspension of 8.7 g (81.9 mmol) of sodium carbonate in 5.3 g (117.8 mmol) of dimethylamine and 50 ml of 1,2-dichloroethane. The mixture is left for 25 hours at room temperature and then evaporated at 50° C. in vacuo. The residue is suspended in 300 ml of water, extracted four times with methylene chloride/ethanol (4:1) and the combined organic extracts are subsequently dried and evaporated. Crystallisation from methylene chloride/ethyl acetate yields 3-[6-(o-chlorophenyl)-4H-s-triazolo[4,3- a][1,4]benzodiazepin-8-yl]-1,1-dimethylurea of melting point 180° C. (decomposition).

EXAMPLE 9

To a solution of [6-(o-chlorophenyl)-1-methyl-4H-s-triazolo[4,3-a][1,4]benzodiazepin-8-yl]isocyanate, prepared as described in paragraph (a) of Example 1 from 7.0 g (21.6 mmol) of 8-amino-6-(o-chlorophenyl)-1-methyl-4H-s-triazolo[4,3-a][1,4]benzodiazepine, but using methylene chloride in place of 1,2-dichloroethane, is added in one portion while stirring and cooling with ice a suspension of 8.7 g (81.9 mmol) of sodium carbonate in 4.2 ml (35.4 mmol) of ethanolamine and 60 ml of acetonitrile. The mixture is left for 27 hours at room temperature and then concentrated at 50° C. in vacuo. The residue is suspended in methylene chloride, the solid is filtered off under suction and recrystallised from ethanol. There is thus obtained 1-[6-(o-chlorophenyl)-1-methyl-4H-s-triazolo[4,3-a][1,4]benzodiazepin-8-yl]-3-(2-hydroxyethyl)urea of melting point 188° C. (decomposition).

EXAMPLE 10

A solution of [6-(o-chlorophenyl)-1-methyl-4H-s-triazolo[4,3-a][1,4]benzodiazepin-8-yl]isocyanate, prepared as described in paragraph (a) of Example 1 from 7.0 g (21.6 mmol) of 8-amino-6-(2-chlorophenyl)-1-methyl-4H-s-triazolo[4,3-a][1,4]benzodiazepine, but using methylene chloride in place of 1,2-dichloroethane, is treated while stirring and cooling with ice with a suspension of 8.7 g (81.9 mmol) of sodium carbonate in 50 ml of ice-cold methylene chloride and 5 g (111.1 mmol) of dimethylamine, the suspension being added in one portion. After the addition of 60 ml of dry acetonitrile, the mixture is stirred at room temperature for 20 hours and concentrated at 50° C. in vacuo. The residue is suspended in 100 ml of methylene chloride and 100 ml of water and filtered off. The material remaining is dissolved in 80 ml of hot ethanol and left to stand at −10° C. overnight. After filtering off the resulting crystals, there is obtained 3-[6-(o-chlorophenyl)-1-methyl-4H-s-triazolo[4,3-a][1,4]-benzodiazepin-8-yl]-1,1-dimethylurea of melting point 186° C. (decomposition).

EXAMPLE 11

(a) A solution of [6-(o-chlorophenyl)-1-methyl-4H-s-triazolo[4,3-a][1,4]benzodiazepin-8-yl]isocyanate is prepared as described in paragraph (a) of Example 1 from 7.0 g (21.6 mmol) of 8-amino-6-(o-chlorophenyl)-1-methyl-4H-s-triazolo[4,3-a][1,4]benzodiazepine, but using methylene chloride in place of 1,2-dichloroethane.

(b) The foregoing isocyanate solution is treated while stirring and cooling with ice with a suspension of 8.7 g (81.9 mmol) of sodium carbonate in 5.9 ml (70 mmol) of pyrrolidine and 60 ml of acetonitrile. The mixture is stirred at room temperature for 68 hours and concentrated at 50° C. in vacuo. The residue is extracted twice with 500 ml of methylene chloride/ethanol (4:1) each time. The organic phases are washed with 3 N hydrochloric acid and water, dried and evaporated. The residue, after recrystallisation from 400 ml of methylene chloride, gives N-[6-(o-chlorophenyl)-1-methyl-4H-s-triazolo[4,3-a][1,4]benzodiazepin-8-yl]-1-pyrrolidinecarboxamide which melts at 188° C. (decomposition).

EXAMPLE 12

(a) From 55 g (0.2 mmol) of 2-amino-5-nitro-2'-chloro-benzophenone there is obtained in analogy to the procedure described in paragraphs (a) and (b) of Example 4 5-(o-chlorophenyl)-1,3-dihydro-3,3-dimethyl-7-nitro-2H-1,4-benzodiazepin-2-one which, after recrystallisation from methylene chloride/hexane, melts at 242° C.

(b) In analogy to the procedure described in paragraph (c) of Example 4, from 20 g (58 mmol) of 5-(o-chlorophenyl)-1,3-dihydro-3,3-dimethyl-7-nitro-2H-1,4-benzodiazepin-2-one there is obtained 6-(o-chlorophenyl)-1,4,4-trimethyl-8-nitro-4H-s-triazolo[4,3-a][1,4]benzodiazepine which, after recrystallisation from ethanol, melts at 283° C.

(c) In analogy to the procedure described in paragraph (d) of Example 4, from 48.5 g (0.127 mmol) of the product of paragraph (b) there is obtained 8-amino-6-(o-chlorophenyl)-1,4,4-trimethyl-4H-s-triazolo[4,3-a][1,4]benzodiazepine. After recrystallisation from ethanol, this product melts at 289° C.

(d) From a solution of [6-(o-chlorophenyl)-1,4,4-trimethyl-4H-s-triazolo[4,3-a][1,4]benzodiazepin-8-yl]isocyanate, prepared as described in paragraph (a) of Example 1 from 7 g (19.9 mmol) of 8-amino-6-(o-chlorophenyl)-1,4,4-trimethyl-4H-s-triazolo[4,3-a][1,4]benzodiazepine, but using methylene chloride in place of 1,2-dichloroethane, there is obtained in analogy to the procedure described in paragraph (b) of Example 7 1-[6-(o-chlorophenyl)-1,4,4-trimethyl-4H-s-triazolo[4,3-a][1,4]benzodiazepin-8-yl]-3-(2-hydroxyethyl)urea which, after recrystallisation from toluene/ethanol, melts at 218°-220° C.

EXAMPLE 13

(a) In analogy to the procedure described in paragraph (a) of Example 5, from 53.6 g (0.15 mol) of 5-(o-chlorophenyl)-1,3-dihydro-3,3-dimethyl-7-nitro-2H-1,4-benzodiazepin-2-one [Example 12, paragraph (a)] there is obtained 6-(o-chlorophenyl)-4,4-dimethyl-8-nitro-4H-s-triazolo[4,3-a][1,4]benzodiazepine which, after recrystallisation from ethanol, melts at 262° C.

(b) In analogy to the procedure described in paragraph (b) of Example 5, from 21.2 g (57 mmol) of the product of paragraph (a) there is obtained 8-amino-6-(o-chlorophenyl)-4,4-dimethyl-4H-s-triazolo[4,3-a][1,4]benzodiazepine which, after recrystallisation from ethyl acetate, melts at 264° C.

(c) From a solution of [6-(o-chlorophenyl)-4,4-dimethyl-4H-s-triazolo[4,3-a][1,4]benzodiazepin-8-yl]isocyanate, prepared as described in paragraph (a) of Example 1 from 7 g (20.7 mmol) of the product of paragraph (b), but using methylene chloride in place of 1,2-dichloroethane, there is obtained in analogy to the procedure described in paragraph (b) of Example 11 N-[6-(o-chlorophenyl)-4,4-dimethyl-4H-s-triazolo[4,3-a][1,4]benzodiazepin-8-yl]-1-pyrrolidinecarboxamide which, after recrystallisation from methylene chloride, melts at 253° C.

EXAMPLE 14

From 7.0 g (20.9 mmol) of 8-amino-6-(o-fluorophenyl)-1,4,4-trimethyl-4H-s-triazolo[4,3-a][1,4]benzodiazepine there is obtained, in analogy to the procedure described in Example 1, via [6-(o-fluorophenyl)-1,4,4-trimethyl-4H-s-triazolo[4,3-a][1,4]benzodiazepin-8-yl]isocyanate, N-[6-(o-fluorophenyl)-1,4,4-trimethyl- 4H-s-triazolo-[4,3-a][1,4]benzodiazepin-8-yl]-1-pyrrolidinecarboxamide. After recrystallisation from ethyl acetate/ethanol, the product melts at 200° C. (decomposition).

EXAMPLE A

1-[6-(o-Fluorophenyl)-1,4,4-trimethyl-4H-s-triazolo-[4,3-a][1,4]benzodiazepin-8-yl]-3-(2-hydroxyethyl)urea can be used as follows as the active ingredient for the manufacture of pharmaceutical preparations:

| (a) | Tablets | Per tablet |
|---|---|---|
| | Active ingredient | 200 mg |
| | Microcrystalline cellulose | 155 mg |
| | Maize starch | 25 mg |
| | Talc | 25 mg |
| | Hydroxypropylmethylcellulose | 20 mg |
| | | 425 mg |

The active ingredient is mixed with half of the microcrystalline cellulose and granulated with a 10 percent solution of hydroxypropylmethylcellulose in a mixture of isopropanol and methylene chloride. The granulate is dried, sieved and mixed with the remainder of the adjuvants. The resulting mixture is pressed on a press to biplanar tablets having a diameter of 12 mm and a break-bar.

| (b) | Capsules | Per capsule |
|---|---|---|
| | Active ingredient | 100.0 mg |
| | Maize starch | 20.0 mg |
| | Lactose | 95.0 mg |
| | Talc | 4.5 mg |
| | Magnesium stearate | 0.5 mg |
| | | 220.0 mg |

The active ingredient is mixed with the adjuvants and sieved. After mixing again, the capsule fill mass obtained is filled into interlocking gelatin capsules of suitable size on a fully automatic capsule filling machine.

What is claimed:

1. A compound of the formula

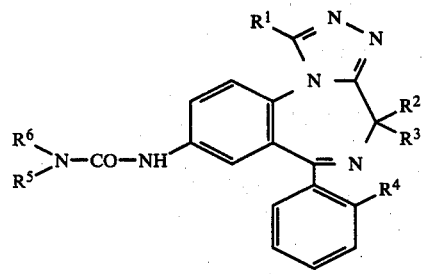

I wherein $R^1$ is a hydrogen atom or a lower alkyl group, $R^2$ and $R^3$ each are a hydrogen atom or a lower alkyl group, $R^4$ is a halogen atom and either $R^5$ is a hydrogen atom or a lower alkyl group and $R^6$ is a lower alkyl or lower hydroxyalkyl group or $R^5$ and $R^6$ together with the nitrogen atom to which they are attached are a 3-membered to 7-membered heterocycle selected from the group consisting of aziridine, pyrrolidone and piperidine, and pharmaceutically acceptable acid addition salts thereof.

2. The compound of claim 1, wherein $R^1$ is a hydrogen atom or a methyl group.
3. The compound of claim 1 or claim 2, wherein $R^2$ and $R^3$ both are a hydrogen atom or both are a methyl group.
4. The compound of claim 3, wherein $R^4$ is a fluorine or chlorine atom.
5. The compound of claim 4, wherein $R^5$ and $R^6$ both are a methyl group or $R^5$ is a hydrogen atom and $R^6$ is a hydroxyethyl group or $R^5$ and $R^6$ together with the nitrogen atom to which they are attached are a pyrrolidinyl group.
6. The compound: 1-[6-(o-Fluorophenyl)-1,4,4-trimethyl-4H-s-triazolo[4,3-a][1,4]-benzodiazepin-8-yl]-3-(2-hydroxyethyl)urea.
7. The compound: 1-[6-(o-Chlorophenyl)-1,4,4-trimethyl-4H-s-triazolo[4,3-a][1,4]-benzodiazepin-8-yl]-3-(2-hydroxyethyl)urea.
8. The compound: 3-[6-(o-Fluorophenyl)-4,4-dimethyl-4H-s-triazolo[4,3-a][1,4]benzodiazepin-8-yl]-1,1-dimethylurea.
9. The compound: 3-[6-(o-Chlorophenyl)-4H-s-triazolo[4,3-a][1,4]benzodiazepin-8-yl]-1,1-dimethylurea.
10. The compound: 3-[6-(o-Chlorophenyl)-1-methyl-4H-s-triazolo[4,3-a][1,4]benzodiazepin-8-yl]-1,1-dimethylurea.
11. The compound: N-[6-(o-Chlorophenyl)-4,4-dimethyl-4H-s-triazolo[4,3-a][1,4]benzodiazepin-8-yl]-1-pyrrolidinecarboxamide.
12. A compound selected from the group consisting of:
   1-[6-(o-Fluorophenyl)-4H-s-triazolo[4,3-a][1,4]benzodiazepin-8-yl]-3-(2-hydroxyethyl)urea,
   3-[6-(o-fluorophenyl)-4H-s-triazolo[4,3-a][1,4]benzodiazepin-8-yl]-1,1-dimethylurea,
   1-[6-(o-fluorophenyl)-1-methyl-4H-s-triazolo-[4,3-a][1,4]benzodiazepin-8-yl]-3-(2-hydroxyethyl)urea,
   3-[6-(o-fluorophenyl)-1,4,4-trimethyl-4H-s-triazolo[4,3-a][1,4]benzodiazepin-8-yl]-1,1-dimethylurea,
   1-[6-(o-chlorophenyl)-4H-s-triazolo[4,3-a][1,4]benzodiazepin-8-yl]-3-(2-hydroxyethyl)urea,
   1-[6-(o-chlorophenyl)-1-methyl-4H-s-triazolo[4,3-a]-[1,4]benzodiazepin-8-yl]-3-(2-hydroxyethyl)urea,
   N-[6-(o-chlorophenyl)-1-methyl-4H-s-triazolo[4,3-a][1,4]benzodiazepin-8-yl]-1-pyrrolidinecarboxamide and
   N-[6-(o-fluorophenyl)-1,4,4-trimethyl-4H-s-triazolo[4,3-a][1,4]benzodiazepin-8-yl]-1-pyrrolidinecarboxamide.

13. A compound of the formula

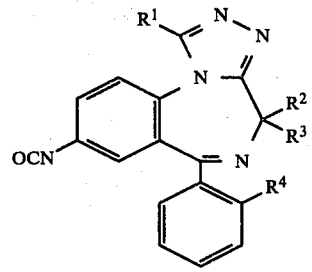

II wherein $R^1$ is a hydrogen atom or a lower alkyl group, $R^2$ and $R^3$ each are a hydrogen atom or a lower alkyl group and $R^4$ is a halogen atom.

14. A compound of the formula

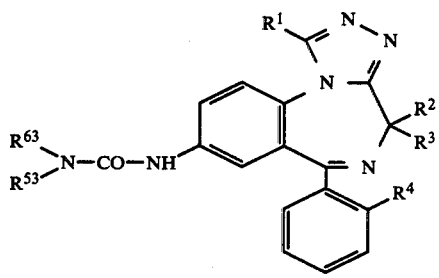

VII wherein $R^1$ is a hydrogen atom or a lower alkyl group, $R^2$ and $R^3$ each are a hydrogen atom or a lower alkyl group, $R^4$ is a halogen atom and either $R^{53}$ is a protecting group and $R^{63}$ is a lower alkyl group or a group of the formula

—A—O—Y  VIII in which A is a lower alkylene group and Y is a protecting group, or $R^{53}$ is a hydrogen atom or a lower alkyl group and $R^{63}$ is as above.

15. A compound of the formula

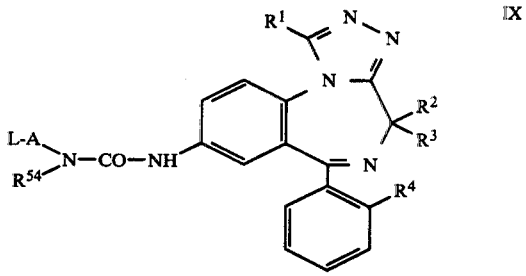

IX wherein $R^1$ is a hydrogen atom or a lower alkyl group, $R^2$ and $R^3$ each are a hydrogen atom or a lower alkyl group, $R^4$ is a halogen atom, A is a lower alkylene group, $R^{54}$ is a hydrogen atom or a lower alkyl group and L is a leaving group.

* * * * *